United States Patent [19]

Leonard et al.

[11] Patent Number: 4,720,266
[45] Date of Patent: Jan. 19, 1988

[54] DENTAL TREATMENT DEVICE

[75] Inventors: Henri Leonard; Bernard Lacour, both of Besancon; Jean-Claude Boinot, Roulans; Jean-Paul Jacoulet, Besancon, all of France

[73] Assignee: Micro-Mega S.A., Besancon, France

[21] Appl. No.: 844,079

[22] Filed: Mar. 26, 1986

[30] Foreign Application Priority Data

Mar. 27, 1985 [FR] France ............................... 85 05016
Mar. 27, 1985 [FR] France ............................... 85 05017
May 6, 1985 [FR] France ............................... 85 07161

[51] Int. Cl.⁴ ............................................. A61C 1/08
[52] U.S. Cl. ............................................. 433/126
[58] Field of Search ........................... 433/126, 29

[56] References Cited

U.S. PATENT DOCUMENTS 4,433,957 2/1984 Nakanishi ........................... 437/126
4,507,085 3/1985 Mosimann et al. ................. 437/126
4,600,384 7/1986 Olsen ................................. 433/29

Primary Examiner—Robert Peshock
Attorney, Agent, or Firm—Emmanuel J. Lobato; Robert E. Burns

[57] ABSTRACT

This device comprises a dental handpiece (15), notably a contra-angle, detachably coupled to a socket (35) so that the handpiece can rotate freely relative to the socket, this socket incorporating a micromotor for driving the dental treatment tool. The handpiece comprises means for illuminating the treatment area and the electric power supply between the two elements is taking place by means of spring loaded contact pistons (19, 22) parallel to the handpiece axis and projecting from the front face of one of the two elements, the contact pistons being adapted, in the coupled condition, to be urged against corresponding annular electric tracks (18, 21) provided at the end of the other element, these tracks being insulated from each other by a ring (20).

2 Claims, 17 Drawing Figures

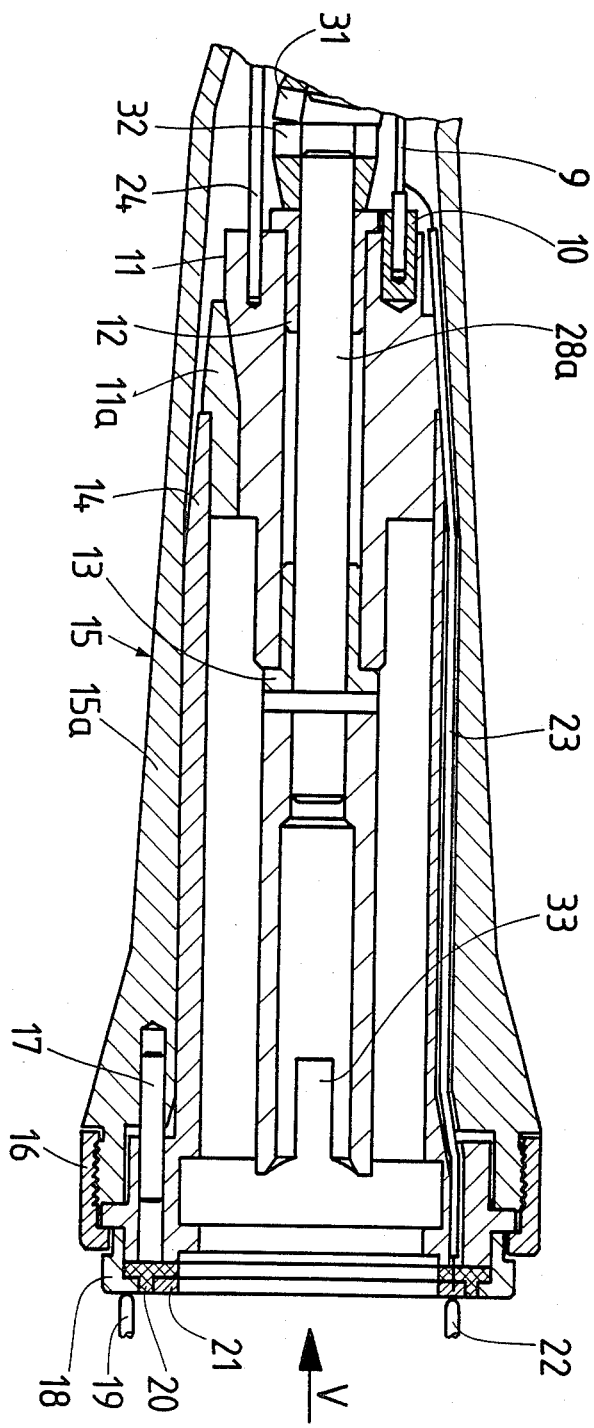

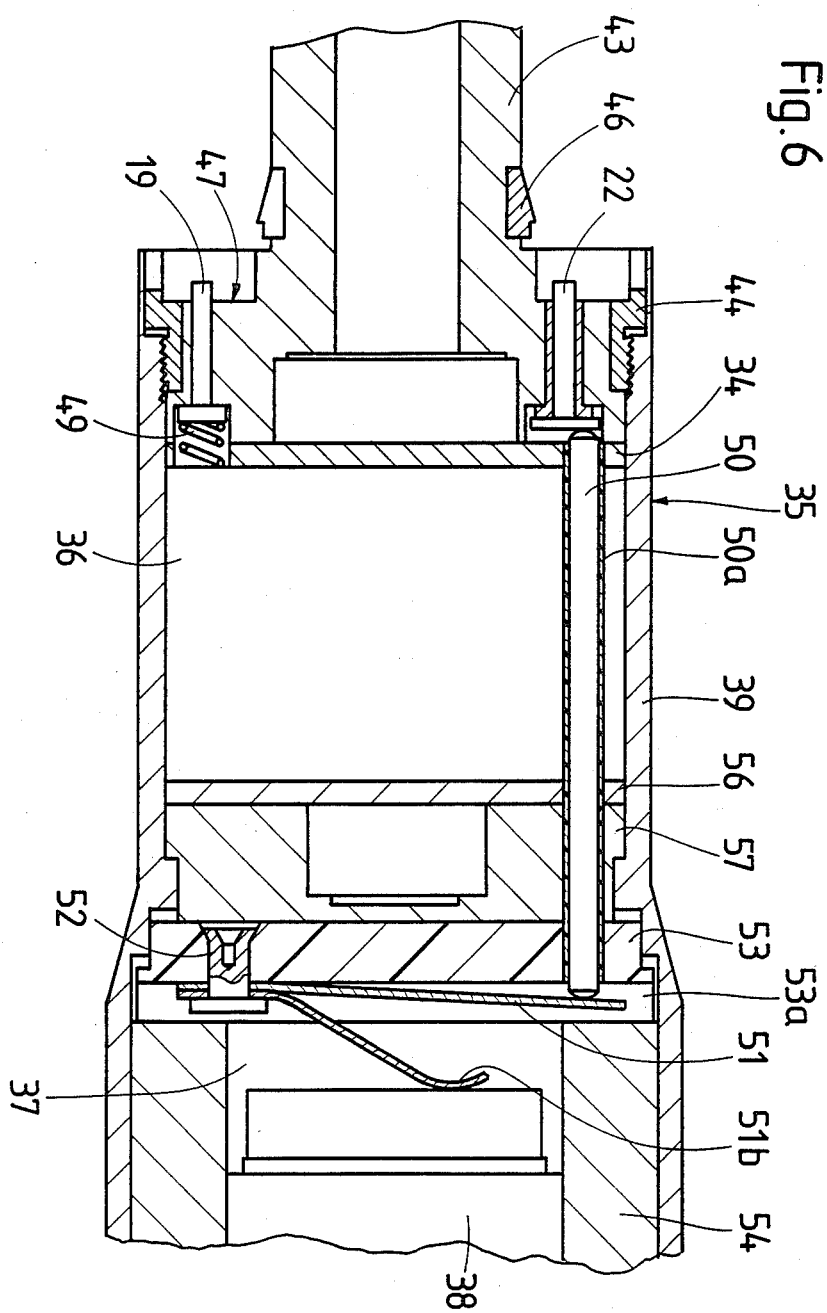

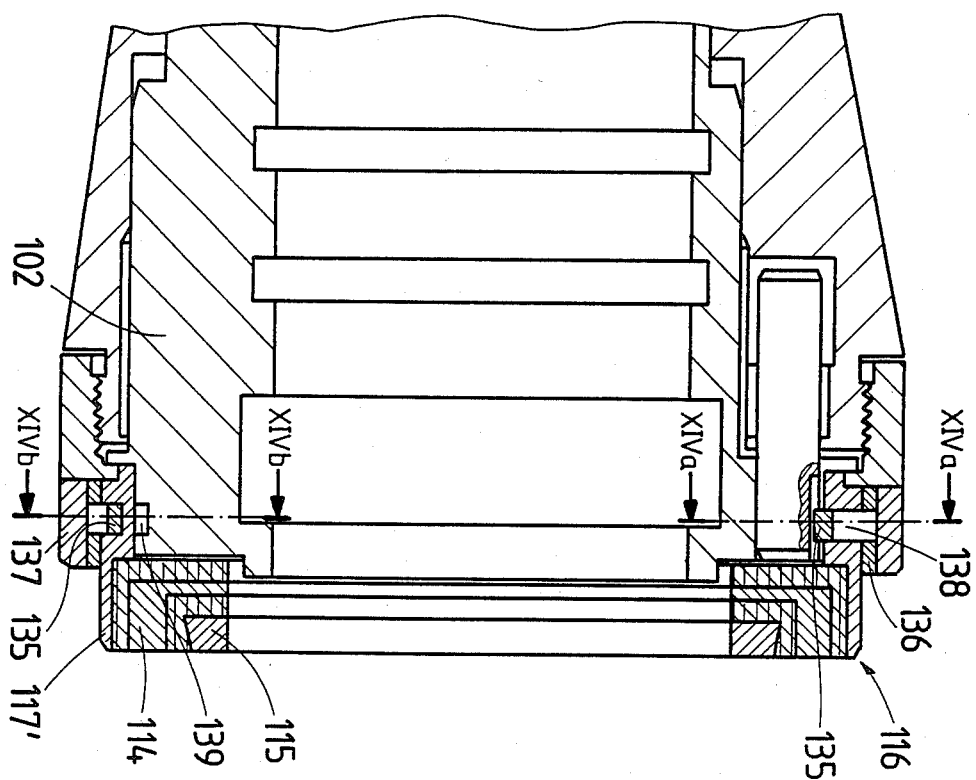

DENTAL TREATMENT DEVICE

The present invention relates to a dental treatment device comprising a handpiece adapted to receive the treatment instrument therein and a socket adapted to be detachably connected to the rear end of said handpiece and which, in the coupled condition, can rotate freely relative to the handpiece, said socket incorporating preferably a micromotor for driving said instrument.

Handpieces of this type are already known in the art, notably through the U.S. Pat. No. 3,432,194, wherein the detachable socket enclosing the means for driving the treatment instrument is coupled to the handpiece in such a manner that the two members can rotate freely in relation to each other. This coupling device is easy to handle, avoids any relaive prepositioning of the members, and more particularly, facilitates the handling of the handpiece by the dental surgeon. In the case of a handpiece driven by a micromotor, said socket encloses a micromotor.

By the way, the general trend in modern handpieces is increasingly towards the incorporation of means for illuminating the treatment area in the patient's mouth, especially in the case of contra-angles. However, if these instruments are to be provided with a coupling device of the above-mentioned type, a problem arises when designing the electrical connection between the socket and the handpiece, for this electrical connection must be easily disconnectable when uncoupling the component elements while permitting an efficient and easy contact in the coupled condition thereof, without interfering with the free relative rotation of these component elements.

Moreover, the component elements of the electrical connections must necessarily be strong enough to withstand without any damage the frequent daily pleaning and dismantling of the handpiece, and also the severe condition of use.

It is a known proposition in the field of dental equipments to provide dental treatment devices comprising rotary-contact electrical connections or couplings.

For example, in the European Patent Application EP No. 0143985 there is described a rotary coupling device comprising annular tracks cooperating with resilient contact blades obtained by bending metal strips. A connector of this type is strictly limited to an electrical connection of the permanent type, that is, not liable to be frequently connected and disconnected at a high recurrent rate. In fact, the thin metal blades utilized in devices of this character are extremely fragile and liable to deteriorate rapidly. In addition, a cleaning operation performed in the area of these blades would led to a detrimental distortion thereof involving either a poor contact or the risk of short-circuits.

It is the primary object of the present invention to provide a dental treatment device of the type broadly set forth hereinabove, which comprises a light source in the handpiece with an electrical connector that can easily be connected or disconnected when coupling or uncoupling the elements, without interfering with the free rotation of the component elements in relation to each other, this connector being furthermore capable of withstanding frequent cleaning and dismantling of the handpiece without any damage.

For this purpose, the device according to the present invention is characterized in that, between the adjacent faces of the handpiece and of the socket, respectively, a disconnectable electrical connection means is provided for supplying electric power from said socket to a light source disposed in the handpiece for illuminating the treatment area, and that said electrical connection means comprises, on the front face of one of the two elements, a pair of springloaded contact pistons parallel to the axis said pistons projecting from said front face, and on the front face of the other element a pair of annular concentric electric tracks insulated from each other and engaged, in the coupled condition, by said the two contact pistons respectively.

If desired, the contact pistons may be disposed on the front face of the socket and the tracks may be disposed on the rear face of the handpiece, and vice-versa. However, the first solution is preferred because the contacts are less liable to be damaged during cleaning operations and dental treatments. In fact, the handpiece is exposed to very frequent handlings and sterilizations and if the contact pistons were mounted to this element they would be more exposed to damages. This arrangement is also safer in case of improper tests made by the user of the handpiece on a socket not provided with the proper instrument.

The electrical connection according to the present invention is therefore designated with a view to impart the desired sturdiness to the device so that it can be easily connected and disconnected many times all day long, exposed to the various substances utilized by the dental surgeon during dental treatments of all kinds, and be cleaned at regular intervals without any risk of damage.

Finally, the electrical connection thus obtained is universal and allows a compatibility between component elements, such as handpieces and driving sockets, of various origins.

Preferably, the spring-loaded contact pistons emerge from the end face of one of the two elements in the bottom of an annular recess engageable by the annular electrical conducting tracks carried by the other element, said pistons being shorter than the outer wall surrounding said recess.

This particular form of embodiment is definitely advantageous in that the contact pistons are safely protected against the risk of mechanical damages during the handling of the corresponding component element, preferably the socket, when this element is fitted for example on its front face.

In case of need, it may prove useful to have the two annular tracks formed in a module adapted to fit detachably on the end of the handpiece or of the socket. This specific arrangement with tracks formed on a detachable module may facilitate the manufacture and assembly, and also, when necessary, the replacement of said tracks.

Furthermore, this handpiece-mounted module is also advantageous for another reason. Thus, if the practician were desirous to use this contra-angle with a standard micromotor without any contact for electrically connecting the handpiece bulbs, therefore when it is not contemplated to use lighting means, he could not adopt this solution due to the extra thickness resulting from the presence of the annular tracks which increases the distance between the groove and the rear face of the contra-angle.

Therefore, with this detachable module a handpiece is obtained which can be used either with a special micromotor provided with electric contact means, or with a standard micromotor.

The invention is described hereinafter with reference to various forms of embodiment of the device, illustrated in the accompanying drawings, in which:

FIGS. 4a-7 illustrate as a third exemplary form of embodiment a more detailed arrangement comprising a handpiece with a contra-angle head in which the light source is energized from a battery incorporated in the socket.

FIG. 4a is a longitudinal section showing the front portion of the handpiece.

FIG. 4b is a similar view showing the rear portion of the handpiece.

FIG. 5 is a view taken in the direction of the arrow V of FIG. 4b.

FIG. 6 is a longitudinal section showing the front portion of the socket.

FIG. 7 is a longitudinal section taken along another plane of the rear portion of the socket.

FIG. 14 is an axial section showing the rear end of a handpiece to which a fifth form of embodiment of the module is secured, and FIGS. 14a and 14b are cross-sectional views taken along the lines XIVa—XIVa and XIVb—XIVb of FIG. 13, showing the ring in its locked and release positions, respectively.

Figure 1:
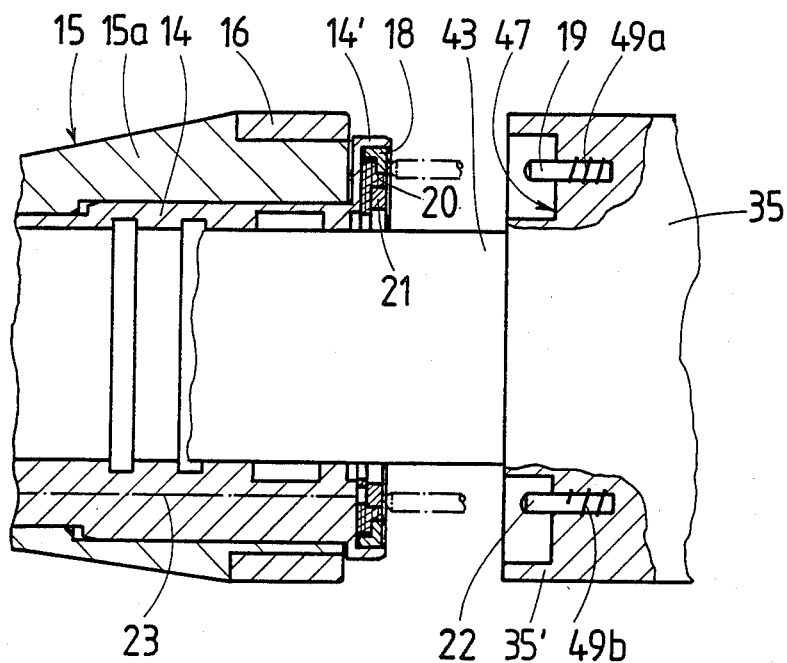
FIG. 1 illustrates in the form of a diagrammatic example the principle of the invention which comprises annular tracks on the handpiece side and contact pistons on the socket.
Figure 2:
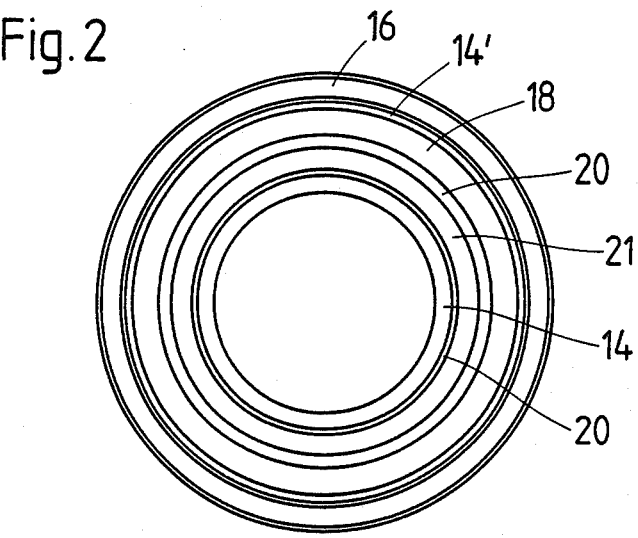
FIG. 2 is an end view showing the rear end of the handpiece.

As shown in FIGS. 1 and 2, the handpiece 15, for example a contra-angle of which only the rear end is shown in FIG. 1, is provided in its head area with a light source consisting of an electric bulb (not shown in the drawing) for illuminating the treatment area at the operative end of the instrument.

The handpiece consists of an external sleeve 15a and of an inner sleeve 14 made of electrically conducting material. Enclosed in the rear end 14' of the inner sleeve 14 are a first electrical annular track 18 contacting said inner sleeve 14 and a second electrical annular track 21 concentric to, and disposed inside, said first annular track 18. Said tracks 18, 21 are electrically insulated from each other by means of an insulating ring 20 also acting as a means for electrically insulating the second annular track 21 from the inner sleeve 14. An insulated conductor 23, shown in dash and dot lines in FIG. 1, interconnects the second annular track 21 and the bulb, while the ground contact is obtained from the first annular track 18 via the inner conducting sleeve 14.

The socket 35, of which the front end is shown only partially, comprises a projecting stub 43 adapted in the coupled condition to engage the bore of the inner sleeve 14, and also means for interconnecting the tool-driving central shaft (not shown) fitted in the handpiece and the source of driving power, for instance a micromotor housed in said socket 35. Le means (not shown in the drawing) for coupling the socket 35 to the handpiece 15 permits a free rotation between these two members and may consist, for example, of the means described in the U.S. Pat. No. 3,432,194.

The front face of socket 35 is provided with an annular recess 47 adapted, when the handpiece is fitted to the socket 35, to be engaged by the rear end 14' of the inner sleeve 14, and by the annular tracks 18 and 21 of handpiece 15. A ring 16 fitted on the outer sleeve 15a of handpiece 15 keeps the two members in proper axial alignment. Projecting from the bottom of this annular recess 47 are contact pistons 19, 22 parallel to the socket axis and slidable in the axial direction. These contact pistons 19, 22 are responsive to springs 49a and 49b, respectively, and shifted radially from each other. Contact 19 is grounded and contact 22 is connected to the other terminal of the source of electric power. In the coupled condition of the component elements these contact pistons 19 and 22, respectively, are urged against the corresponding annular tracks 18 an 21, respectively, of handpiece 15, and can easily slide thereon during the relative rotation of said members. The wall 35' of socket 35 which surrounds the recess 47 is longer than the projecting portion of contact pistons 19, 22 in order to properly protect these pistons.

The contact pistons 19, 22 are supplied with electric current either from batteries housed in said socket 35 or from an external source of current via electric wires extending through said socket.

As already mentioned hereinabove, the socket incorporates preferably and electric or pneumatic micromotor, but the handpiece may also be driven in the conventional manner by means of an external motor via a belt and pulley transmission, and in this case the socket incorporates the elements for converting the movement. The handpiece may also be of the turbine type.

Figure 3:
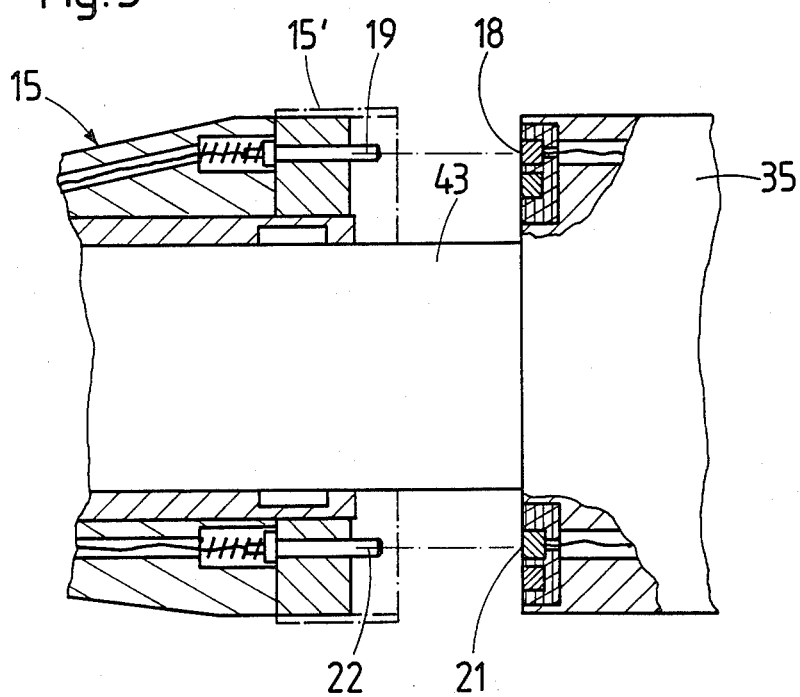
FIG. 3 is a view similar to FIG. 1 showing an inverted arrangement of the tracks and contact pistons.

In FIG. 3, and inverted arrangement of the contact elements is shown, namely, the annular electric tracks 18, 21 are provided on the front face of socket 35 whereas the contact pistons 19, 22 are mounted to the rear face of handpiece 15. Also in this case, means for protrecting the contact pistons 19, 22, for example in the form of a ring 15' rigid with handpiece 15 and protruding axially beyond the contact pistons, may be provided.

Figure 4A:
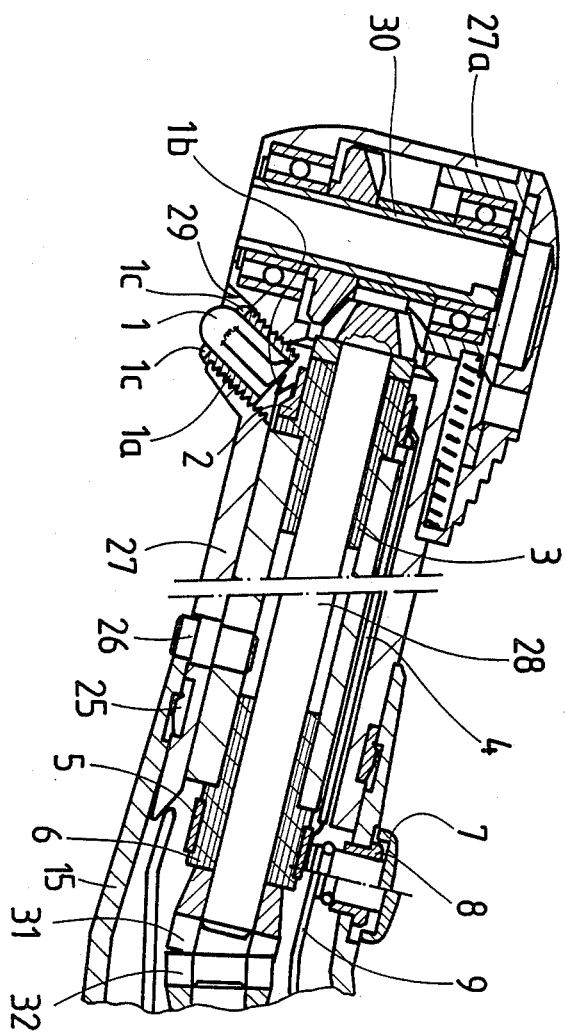

FIGS. 4a and 4b illustrate more in detail a contra-angle handpiece according to a third form of embodiment. This handpiece consists in the known fashion of a handle 15 and a front section 27 incorporating the head 27a in which an instrument (not shown) is adapted to be fitted in a tool holder 30. This tool holder 30 is driven as conventional by a rotary shaft 28 housed in the front section 27 and provided at its rear end with a pinion 31 adapted to mesh with a corresponding pinion 32 rigid with the front end of another shaft 28a rotatably mounted in said handle 15. This shaft 28a, in the example illustrated, is adapted to be driven by a micromotor housed in a socket 35 (FIGS. 6 and 7), which can be secured to the rear and of handle 15. In this case, the nose of the micromotor protrudes into the handle, and its output shaft is in driving engagement with the fork 33 formed at the rear and of shaft 28a. The front section 27 is force fitted in the external sleeve 15a of handle 15 and rigidly connected thereto by means of a circlip 25 and positioned circonferentially by a radial pin 26 secured to the body of the head.

A cavity 29 formed in the body of head 27a is adapted to receive an electric bulb 1 cemented or crimped in a conducting holder 1a screwed in the body of head 27a. This holder 1a has two diametral slots 1c formed therein so that it can be screwed in or out by means of a suitable screwdriver. The angle of inclination of said cavity 29 relative to the tool axis is such that the light rays emitted by the bulb 1 are directed towards the treatment area at the tool end. The ground terminal of bulb 1, that is, the external socket of the bulb base, is held in close contact, for example by welding, with the bulb holder 1a engaging in turn the body of the group-forming front section 27 also made from a suitable conducting metal. The other terminal 1b of bulb 1, which is the central contact of the bulb base, engages a metal ring 2 crimped on a support 3 of insulating material acting as a front bearing or supporting a bearing in which the shaft 28 is rotatably mounted. This ring 2 is supplied with electric current through an insulated wire 4 having one end welded to said ring 2 and its other end welded to another metal ring 5 crimped in turn to another insulating support 6 acting as a rear bearing or supporting another bearing for shaft 28.

Since the front section 27 must be separable from the handle 15, the current is fed to this second ring 5 via a resilient contact 9 consisting of a spring blade having one end embedded in an inner conducting sleeve 11 forming a part of handle 15. This resilient contact 9 extends axially in the handle 15 and can be caused to contact the ring 5 at will through a switch 7 consisting of a push-knob, which is slidably fitted in a ring 8 embedded in turn in the body of the external sleeve 15a of handle 15. The push-knob head is mushroom-shaped to prevent the ingress of dust and foreign substances in the contra-angle. When the push-knob 7 is depressed by one of the fingers of the user's hand holding the handpiece, the spring blade 9 is deflected and move towards the ring 5, thus closing the contact. Therefore, the dental surgeon can turn the light on when necessary, and notably without necessarily actuating the tool at the same time. The circuit is opened automatically when the contra-angle is released, the pushknob being restored automatically to its inoperative position by the spring blade 9 acting as a return spring. Thus, the operator is assured that when the contra-angle is not in use the bulb will remain deenergized.

The spring blade 9 is supplied with current by means of an insulated conducting wire 23 housed in a groove formed in another inner sleeve 14 of conducting metal. The front end of wire 23 is wended to the spring blade 9 and its rear end is in electric contact with an annular conducting track 21 surrounding concentrically the shaft 28a and constituting the rear end of the handle.

Figure 5:
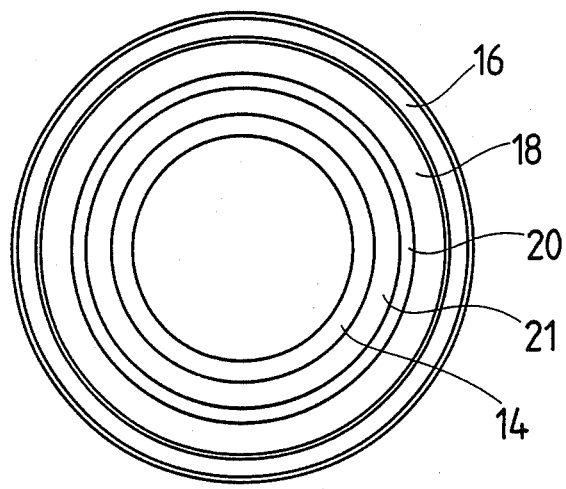

The other electric line constituting the ground consists of the inner sleeves 11, 14 of conducting metal which are fitted in the handle 15. The sleeve 11 is forcefitted in said sleeve 14 slide-fitted in turn in the external sleeve 15a, and secured thereto by means of a rear nut 16 locked against rotation by a pin 17. On the rear surface of handle 15 the ground line terminates with an annular track 18 consisting of a metal ring surrounding concentrically the other annular track 21 and secured to the sleeve 14 so as to hold in position an insulating ring 20 separating said metal ring from said track 21 (FIGS. 4b and 5).

Mounted in the sleeve 11 are two bearings 12, 13 in which the shaft 28a is rotatably mounted. In addition, an orifice is formed in sleeve 11 in case the circulation of a cooling fluid were contemplated; in the example illustrated, this orifice is closed by a metal plug 11a. The outer sleeve 15a is made for example of aluminum alloy.

To ensure an efficient contact between the conducting body of the front section 27 and the sleeve 11 of handle 15, a resilient contact 24 is provided, for example in the form of a rod forcefitted in sleeve 11 and curved so as to constantly engage a bevelled portion of the body of the front section 27 for deflecting the rod 24 and thus provide a good electrical contact.

Thus, a simple electrical connection is obtained between the two sections of the contra-angle while permitting the easy and quick assembly and disassembly thereof by simply pulling the front section 27 out of handle 15, this movement causing the circlip 25 to yield inwardly, and the extracting from the handle 15 the complete assembly enclosed in sleeve 14 by unscrewing the nut 16. Moreover, the same handle 15 can be used with different heads.

The handpiece is adapted to be driven from a suitable pneumatic or electric micromotor housed in a socket 35 (FIGS. 6 and 7) connectable to the rear end of handle 15 and comprising two contacts 19 and 22, respectively, consisting of spring-loaded pistons and adapted to engage the annular tracks 18 and 21, respectively, of said handle. The source of electric current for energizing the bulb 1 is a rechargeable battery 38 housed in said socket 35.

Figure 7:
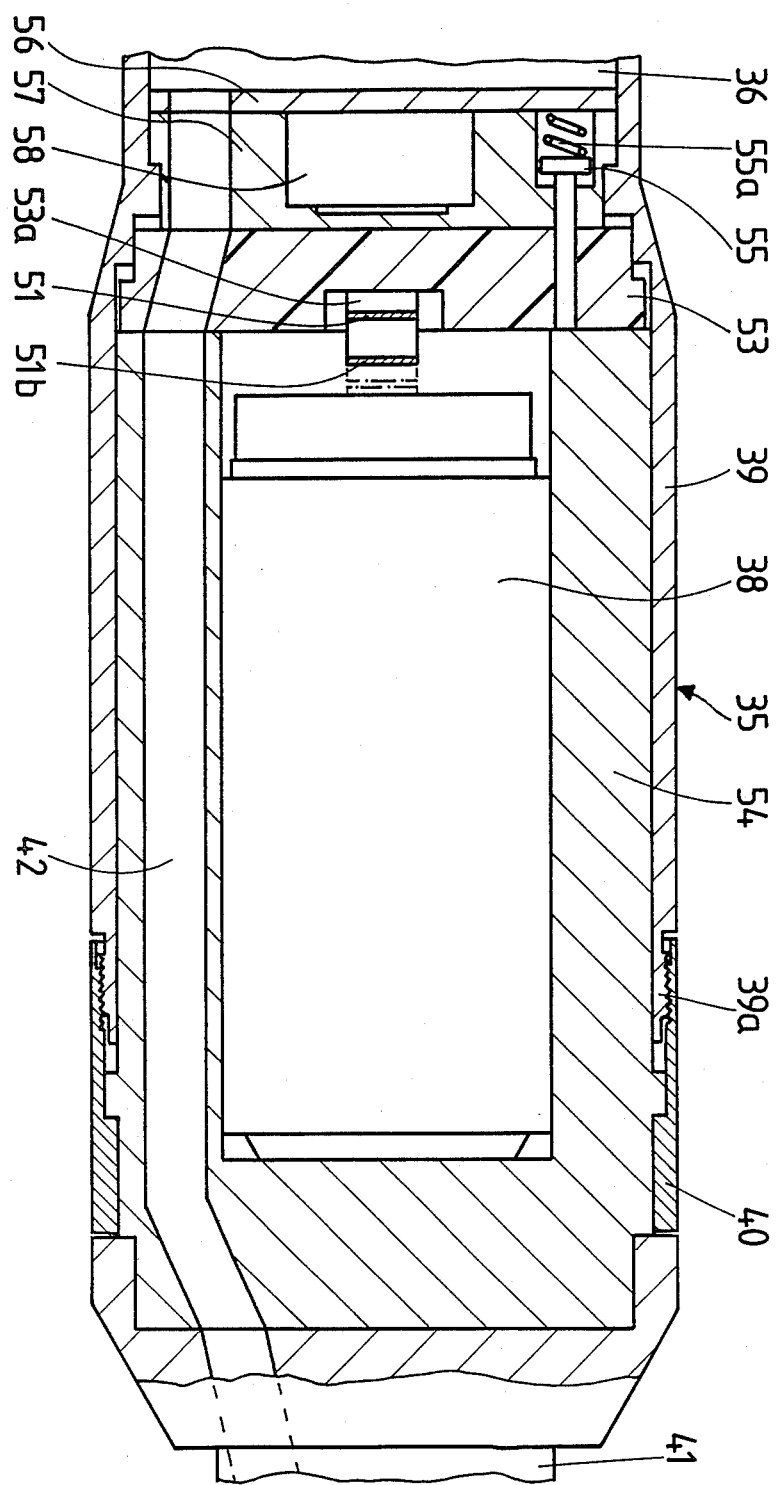

FIGS. 6 and 7 illustrate a form of embodiment of the socket 35 housing the motor unit 36 disposed between cross-plates 34 and 56, and provided behind this motor unit 36 with a cavity 37 adapted to receive the battery 38. In this example the battery 38 houses in cavity 37 has a diameter of about 16 mm and a length of about 32 mm. This 6-Volt battery is capable of supplying a sufficiently bright light during ca. 2 hours.

The socket 35 consists of a front sleeve 39 having a screw-threaded rear end 39a adapted to be engaged by an internally-threaded rear sleeve 40 provided with a ring 41 for coupling this rear sleeve to a supply hose. In the form of embodiment, illustrated the motor 36 is a pneumatic motor of known type having its blades driven by compressed air supplied from an external compressor via the coupling ring 41 and two-way ducts 42 (FIG. 7).

The socket 35 is provided at its front portion with a hollow projection 43 secured at its front end by means of a nut 44. This projection 43, consisting of the nose of the micromotor, and through which the micromotor shaft extends, is adapted to be inserted into the rear end of handle 15 and secured thereto by a spring-loaded hook 46 of known type. The front face of socket 35 comprises an annular recess 47 in which the annular tracks 18, 20 of handle 15 are adapted to be fitted when the handpiece is coupled to the socket. The contact pistons 19, 22 consisting of piston-like rods responsive to spring means emerge from the bottom of said annular recess 47. In this specific form of embodiment, the annular tracks 18 and 21 are also provided on the handpiece side, a provision advantageous in that it avoids the risks of damaging the contact pistons when handling the instrument or during its sterilization.

The ground contact 19 urged by spring 49 projects on the outer side of annular recess 47 so as to register with the annular track 28, and contact 22 projects on the inner side of annular recess 47 so as to register with the other annular track 21 of handle 15.

The rear portion of contact 22 bears against a conducting rod 50 insulated by a sheath 50a. This rod is slidably mounted in a passage formed through cross plate 34, motor unit 36, cross plate 56, an insulating ring 53 and the rear bearing mount 57 (shown only diagrammatically) supporting the rear bearing 58 of the motor. The rear end of rod 50 bears against a resilient blade 51 of conducting metal, housed in a groove 53a formed in the insulating ring 53. The resilient blade 51 is connected by a rivet 52 to another resilient blade 51b that provides the contact with the positive terminal of battery 38, said rivet 52 being clinched in the insulating ring 53. The resilient blade 51 exerts an axial resilient pressure against sliding rod 50 pressed in turn against contact 22, so that this contact 22 is constantly urged resiliently outwards.

The other spring-loaded contact 19 (FIG. 6) contituting the ground contact is fed with energizing current via the battery supporting sleeve 54 which, when sleeves 39 and 40 (FIG. 7) are screwed together, engages a contact 55 urged by a spring 55a. This contact 55 bears against the metal cross-plate 56 engaging in turn a portion of motor unit 36 of conducting metal in order to establish an electric connection with the spring-loaded contact 19.

Several forms of embodiment of the device incorporating contact tracks carried by a detachable module will now be described with reference to FIGS. 8-14.

The handpiece of which only the rear portion is shown in the FIGS. 8-14 comprises an external sleeve 101 in which an inner sleeve 102 is fitted, both sleeves being interconnected by means of a nut 103 screwed on the external sleeve 101. These sleeves 101 and 102 are positioned relative to each other by an eccentric pin 104 driven through the inner sleeve 102 and engaging a notch 105 formed in the external sleeve 101. This handpiece is intended for operation with a micromotor 106 having a nose portion 107 fitting in the bore 108 of inner sleeve 102. This nose portion 107 spring-urged catch 109 adapted to retract during the coupling movement and to spring out at the end of this movement for engaging a groove 110 formed in the inner sleeve 102, in order to provide a rotary coupling between the two sleeves.

Figure 8:
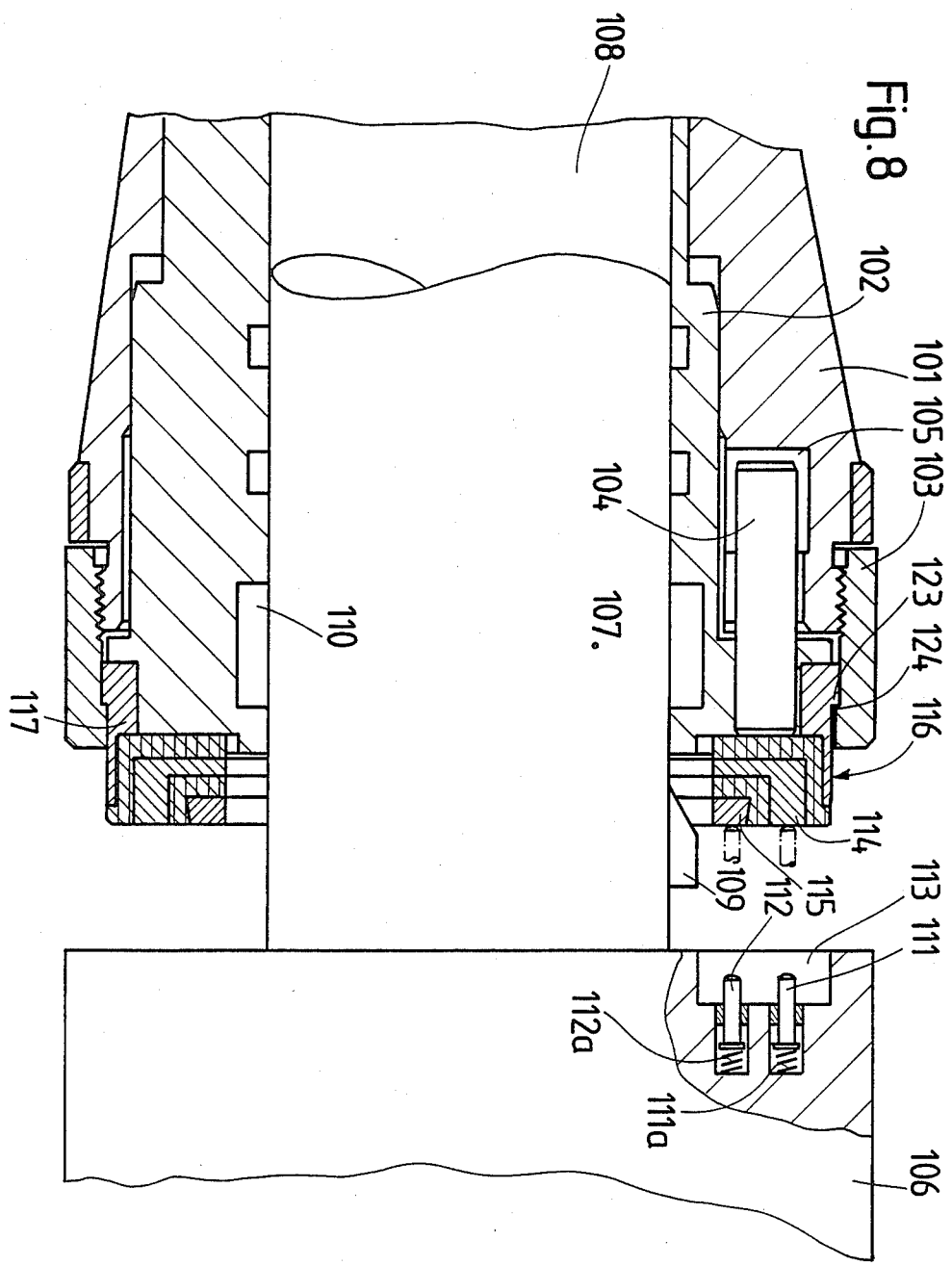
FIG. 8 is an axial section showing a fourth form of embodiment of the rear end of the handpiece, on which a module provided with electric contact tracks is secured and wherein the nose of the special micromotor is partially inserted.

As shown in FIG. 8, the micromotor 106 is provided with contact pistons 111, 112 responsive to springs 111a, 112a for supplying electric current to a device for illuminating the working area at the front end of the handpiece. The contact pistons 111, 112 are disposed in the bottom of an annular recess 113 formed on the front face of the micromotor, as shown in FIG. 8. These pistons 111, 112 are adapted, when the handpiece is coupled to the mocromotor, to engage concentric annular electric tracks 114, 115 fitted in a module 116 adapted to be detachably mounted to the rear end of the handpiece. This module 116, shown separately in FIG. 10, comprises a ring 117 having an annular recess 118 formed therein for receiving a tight-fitting member 119 of insulating plastic material in which the annular electric tracks 114 and 15 are embedded by molding. The tracks 114, 115 are flush with the outer face of plastic member 119 and have their opposite ends welded to plugs 121, 122 contacting lead wires (not shown) supplying electric current to the lighting device.

Various forms of embodiment of the means for fixing the module to the handpiece may be contemplated.

In a first form of embodiment, shown in FIG. 8, these fixing means comprise a shoulder 123 formed externally of the free end of ring 117 and abutting a shoulder 124 formed in nut 103. Thus, when the nut 103 is screwed on the handpiece the module 116 is locked to the hand piece.

Figure 9:
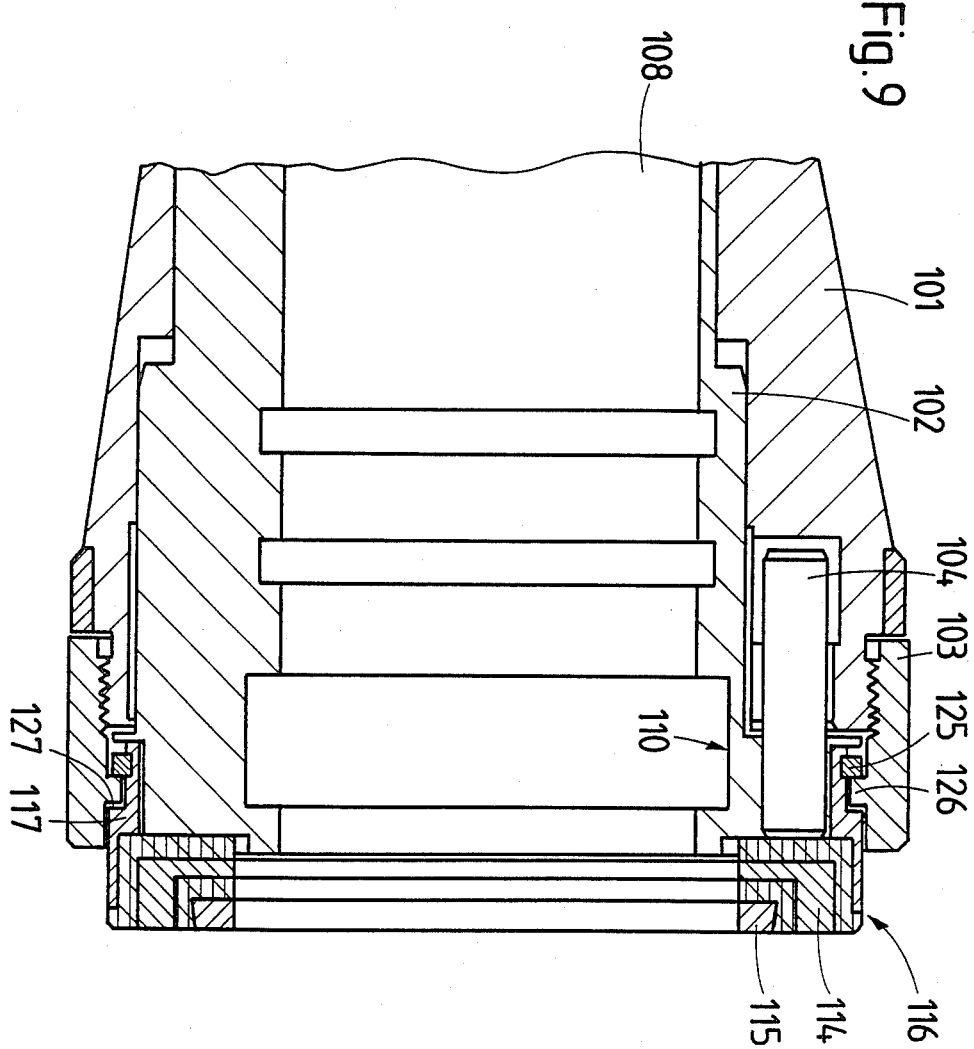
FIG. 9 is an axial section showing the rear end of the handpiece to which a second form of embodiment of the module is secured.
Figure 10:
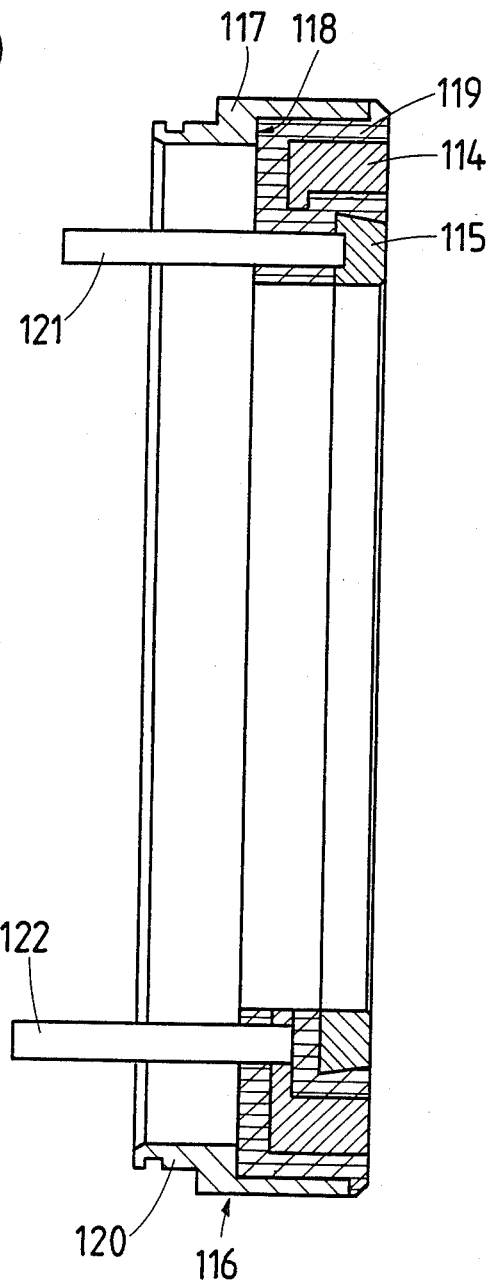
FIG. 10 illustrates in a different axial section the module of the second form of embodiment, shown separately.

FIG. 9 illustrates a second form of embodiment of the means for fixing the module 116. In this case, the means comprise a circlip 125 fitted in a groove at the free end of ring 117 and the nut comprises an annular innerib 126 for retaining the nut between the circlip 125 and a shoulder 127 of ring 117. When the nut 103 is screwed on the external sleeve 101 of the handpiece, the module 116 is locked on the handpiece by the engagement of rib 126 against the circlip 125, and when the nut 103 is released the module 116 can move backwards since it is driven by the rib 126 engaging the shoulder 127.

Figure 12:
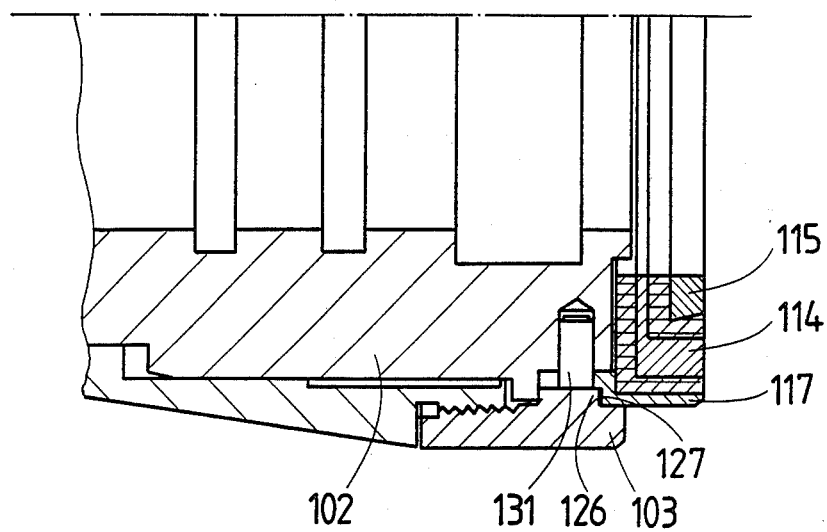
FIG. 12 is an axial sectional view of the rear end of a handpiece to which a third form of embodiment of the module is secured.
Figure 12A:
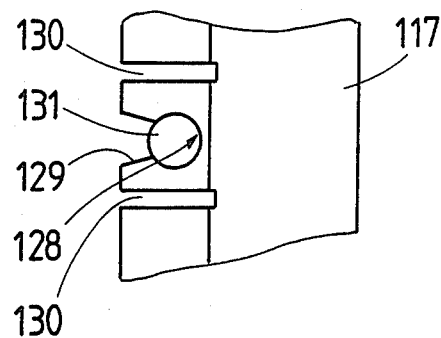
FIG. 12a is a detail view showing the means for securing this third form of embodiment.

In a third form of embodiment, shown in FIGS. 12 and 12a, of the module fixing means, the ring 117 is provided with a circular notch 128 opening through a slot 129 on the free end of the ring, annular slots 130 being provided preferably on either side of this notch for increasing the resiliency of the device. This notch 128 is adapted to receive a pin 131 driven into the inner sleeve 102 of the handpiece. If desired, several pins 131 may be provided on sleeve 102 and several notches 128 on ring 117.

As in the preceding form of embodiment, the notch 103 comprises an inner annular rib 126 engaged by a shoulder 127 of ring 117 so that when it is desired to remove the module 116 it is only sufficient to unscrew the nut 103 so that this nut will push the ring 117 backwards to release the pin 131 from notch 128.

Figure 13:
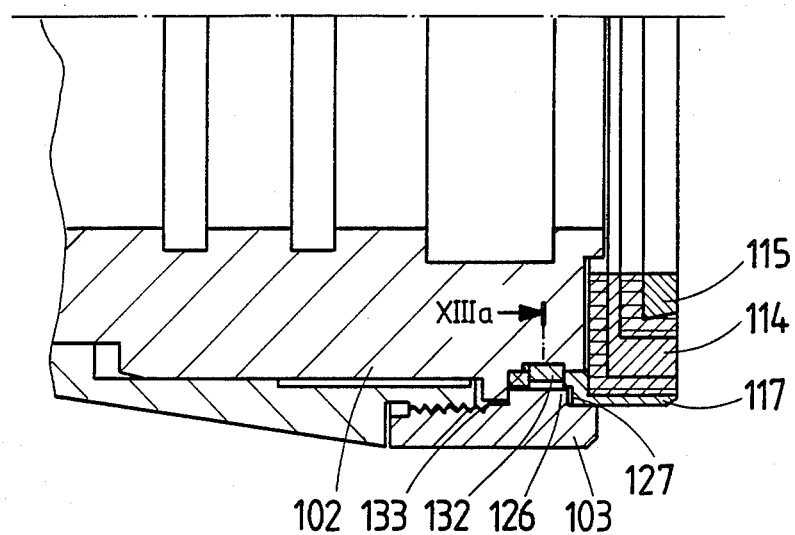
FIG. 13 is an axial section showing the rear end of a handpiece to which a fourth form of embodiment of the module is secured.
Figure 13A:
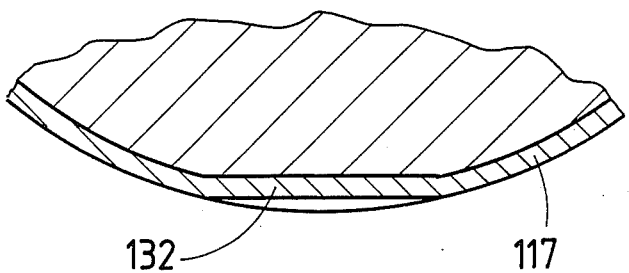
FIG. 13a is a fragmentary section view showing the tongue, the section being taken along the line XIIIa of FIG. 13.

In a fourth form of embodiment illustrated in FIGS. 13 and 13a, the ring 117 comprises in its cylindrical portion surrounding the inner sleeve 102 three resilient tongues 132 having a radially cut-out portion, disposed at spaced intervals along the periphery of ring 117, and depressed radially inwards as shown in FIG. 13a. These tongues 132, in the locking position, engage matching notches 133 formed on the inner sleeve 102. Thus, in these notches 133 the tongues 132 act as circlip-like elements preventing any longitudinal movement of module 116. The ring 117 consists of a metal having a good elasticity in order to withstand momentary distortions and resume its initial shape like a conventional spring. To disassemble the module 116 from the handpiece it is only necessary to rotate the ring 117 until the tongues 132 are released from notches 133 and free the ring 117. Then, the module can be pulled out from the handpiece, for example by unscrewing the nut 103 which, as in the preceding forms of embodiment, comprises an internal rib 126 engaging a shoulder 127 of ring 117.

Another version of these fixing means is illustrated in FIGS. 14, 14a and 14b. In this case, the tongues 135 are cut in an intermediate ring 136 secured in turn to an external ring 137, the two rings 136, 137 being adapted to rotate on ring 117' of module 116. This module ring 127' is provided with apertures 138 through which, in the locking position shown in FIG. 14a, the tongues 135 are engaged for penetrating into a groove 139 of sleeve 102.

To release the module 116 it is only necessary to rotate the external ring 137 until the tongues 135 are moved out from notches 138, as illustrated in FIG. 14b. Unscrewing the nut 103 also permits of pushing the module 116 outwards.

It would also be possible to limit the rotational movement of the rings in either direction, in the last two forms of embodiment described hereinabove.

Figure 11:
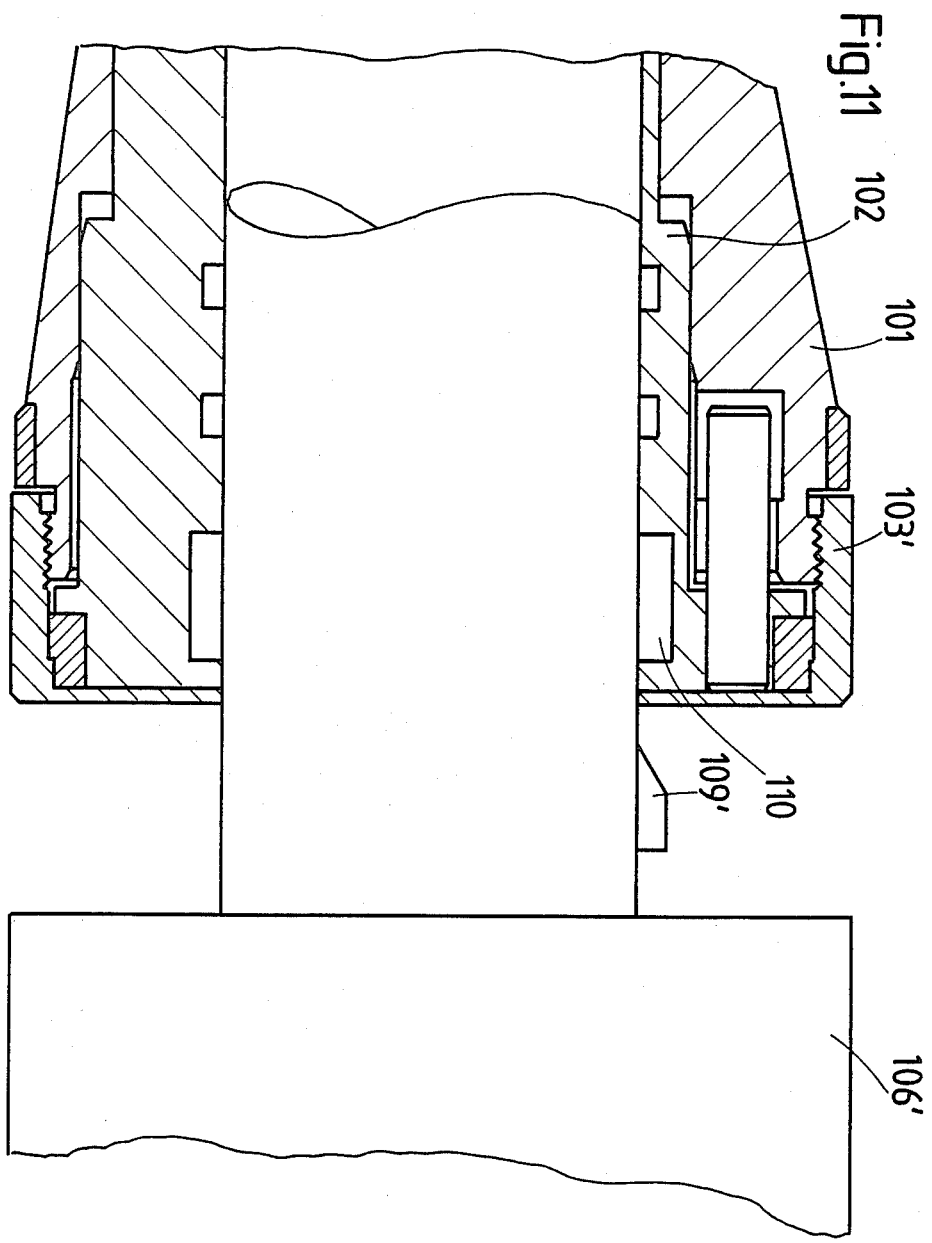
FIG. 11 is an axial section showing the rear end of the handpiece, without the module, in which the nose of a standard mocromotor is inserted.

After removing the module 116, it is possible to use the handpiece with a standardized micromotor 106' as illustrated in FIG. 11. In this case, a cap nut 103' is substituted for nut 103 and the micromotor 106' may be secured normally to the the handpiece by means of the catch 109' and groove 110 system.

Of course, other means for securing the module in the handpiece may be contemplated without departing from the frame of the invention. Obviously, the part to which the module of the handpiece is secured may be inverted, that is, it could also be secured to the socket, and the pistons mounted on the handpiece.

We claim:

1. A dental treatment instrument comprising, a handpiece having a head for mounting a dental tool thereon and having means for illuminating a work area of the dental tool when in use and a micromotor removably mounted on the handpiece, means for establishing an electrical connection between the handpiece and the micromotor comprising a ring module removably mounted on an end of the handpiece and having concentric annular electrical contacts, mounting means for removably mounting the ring module on said handpiece, and the micromotor having housed on an end thereof, and into which end said ring module fits, two resiliently mounted piston-like, electrically conductive contacts for each engaging a respective one of said annular electrical contacts on said ring module mounted on said handpiece for establishing said electrical connection when the handpiece and micromotor are assembled.

2. A dental treatment instrument according to claim 1, in which said ring module comprises a metal ring having an internal cavity in which an insulating plastic body is fitted, said insulating plastic body having said annular electrical contacts embedded therein by molding, and a free end of said ring module dimensioned to fit in said end of said micromotor.

* * * * *

UNITED STATES PATENT AND TRADEMARK OFFICE
CERTIFICATE OF CORRECTION

PATENT NO. : 4,720,266

DATED : Jan. 19, 1988

INVENTOR(S) : Henri Leonard, Bernard Lacour, Jean-Claude Boinot, Jean-Paul Jacoulet It is certified that error appears in the above-identified patent and that said Letters Patent is hereby corrected as shown below: On the title page, Item [30] should read --- Foreign Application Priority Data Mar. 27, 1985 [FR] France..............85 05016
Mar. 27, 1985 [FR] France..............85 05017
May 06, 1985 [FR] France..............85 07161
Dec. 30, 1985 [FR] France..............85 19409    ---.

Signed and Sealed this

Twenty-eighth Day of February, 1989

Attest:

DONALD J. QUIGG

Attesting Officer

Commissioner of Patents and Trademarks